US007431930B2

(12) United States Patent
Mundt et al.

(10) Patent No.: US 7,431,930 B2
(45) Date of Patent: Oct. 7, 2008

(54) INFECTIOUS BURSAL DISEASE VIRUS (IBDV) MUTANT EXPRESSING VIRUS NEUTRALISING EPITOPES SPECIFIC FOR CLASSIC-AND VARIANT IBDV STRAINS

(75) Inventors: Egbert Mundt, Millienhage (DE); Tobias Letzel, Eberswalde (DE); Guntram Paul, Bedburg-Hau (DE); Adriaan Antonius Wilhelmus Maria van Loon, Sambeek (NL)

(73) Assignee: Intervet International B.V., Boxmeer (NL)

( * ) Notice: Subject to any disclaimer, the term of this patent is extended or adjusted under 35 U.S.C. 154(b) by 308 days.

(21) Appl. No.: 10/809,176

(22) Filed: Mar. 24, 2004

(65) Prior Publication Data

US 2005/0058664 A1     Mar. 17, 2005

(51) Int. Cl.
*A61K 39/12* (2006.01)
*A61K 39/295* (2006.01)
*C12N 7/00* (2006.01)

(52) U.S. Cl. .............. 424/204.1; 435/235.1; 424/201.1; 424/202.1

(58) Field of Classification Search .............. 424/204.1, 424/199.1, 192.1; 435/69.1, 235.1, 199.1, 435/252.3
See application file for complete search history.

(56) References Cited

U.S. PATENT DOCUMENTS

| 5,632,989 | A | 5/1997 | Snyder |
| 5,871,744 | A | 2/1999 | Vakharia |
| 6,017,759 | A | * | 1/2000 | Vakharia et al. .............. 435/325 |

FOREIGN PATENT DOCUMENTS

| EP | 0887412 B1 | 10/2003 |
| EP | 1170303 B1 | 6/2006 |
| WO | 9526196 | 10/1995 |

OTHER PUBLICATIONS

Vakharia et al., "Molecular basis of antigenic variation in infectious bursal disease virus" 1: Virus Res. Feb. 1994; 31(2): 265-73.*
Muller et al, "Research on infectious bursal disease-the past, the present and the future," Veterinary Microbiology, 2003.*
Jackwood et al., "Molecular identification of infectious bursal disease virus strains," Avian Dis. Jan.-Mar. 1997; 41(1):97-104.*
Dormitorio et al., "Sequence comparisons of the variable VP2 region of eight infectious bursal disease virus isolates," Avian Dis. Jan.-Mar. 1997;41(1):36-44.*
Jackwood et al., "Identification and comparison of point mutations associated in classic and variant infectious bursal disease viruses," Virus Res. Jun. 1997;49(2):131-7.*
Whetzel et al., "Comparison of neutralizing epitopes among infectious bursal disease viruses using radioimmunoprecipitation," 1: Avian Dis. Jul.-Sep. 1995;39(3):499-506.*

Eterradossi et al., "Critical amino acid changes in VP2 variable domain are associated with typical and atypical antigenicity in very virulent infectious bursal disease viruses," Arch Virol 143, pp. 1627-1636 (1998).*
Yu et al., "Molecular characteristics of full-length genomic segment A of three infectious bursal disease viruses in China: two attenuated strains and one virulent field strain" Avian Dis. Oct.-Dec. 2001;45(4):862-74.*
Boot et al (Journal of Virological Methods 97:67-76, 2001).*
Mundt (Journal of General Virology 80:2067-2076, 1999).*
Lim et al (Journal of Virology 2854-2962, 1999).*
Bayliss, C.D., et al. (1990). A comparison of the sequences of segment A of four infectious bursal disease virus strains and identification of a variable region in VP2. Journal of General Virology, 71:1303-1312.
Bayyari, G.R., et al. (1996). Pathogenicity Studies of an Arkansas Variant Infectious Bursal Disease Virus. Avian Diseases, 40:516-532.
Boot, H.J. et al. (2001). Comparison of RNA and cDNA transfection methods for rescue of infectious bursal disease virus. Journal of Virological Methods, 97:67-76.
Heine, H.G. et al. (1991). Sequence analysis and expression of the host-protective immunogen VP2 of a variant strain of infectious bursal disease virus which can circumvent vaccination with standard type I strains. Journal of General Virology, 72:1835-1843.
Jackwood, D.J. et al. (1997). Identification and comparison of point mutations associated in classic and variant infectious bursal disease viruses. Virus Research, 49:131-137.
Kunkel, T.A. et al. (1987). Rapid and Efficient Site-Specific Mutagenesis without Phenotypic Selection. Methods in Enzymology, 154:367-382.
Lim, B.L. et al. (1999). Adaptation of Very Virulent Infectious Bursal Disease Virus to Chicken Embryonic Fibroblasts by Site-Directed Mutagenesis of Residues 279 and 284 of Viral Coat Protein VP2. Journal of Virology, 73(4), 2854-2862.
Mundt, E. (1999). Tissue culture infectivity of different strains of infectious bursal disease virus is determined by distinct amino acids in VP2. Journal of General Virology, 80:2067-2076.
Mundt, E. et al. (1995). Identification of a novel viral protein in infectious bursal disease virus-infected cells. Journal of General Virology. 76:437-443.
Mundt, E. et al. (1996). Synthetic transcripts of double-stranded Birnavirus genome are infectious. Proceedings of the National Academy of Sciences, 93:11131-11136.
Rosenberger, J.K. et al. (1985). Sentinel Bird Survey of Delmarva Broiler Flocks. Proc. 20th Natl. Meeting on Poultry Health and Condemnations. 94-101.
Snyder, D.B. et al. (1994). Active Cross-Protection Induced by a Recombinant Baculovirus Expressing Chimeric Infectious Bursal Disease Virus Structural Proteins. Avian Diseases. 38:701-707.
Snyder, D.B. et al. (1988). Differentiation of Infectious Bursal Disease Viruses Directly from Infected Tissues with Neutralizing Monoclonal Antibodies: Evidence of a Major Antigenic Shift in Recent Field Isolates. Avian Diseases. 32:535-539.

(Continued)

*Primary Examiner*—Mary E Mosher
(74) *Attorney, Agent, or Firm*—William M. Blackstone; Mark W. Milstead

(57) ABSTRACT

The present invention provides a classic IBDV mutant that additionally comprises virus neutralising epitopes 67 (specific for variant-E IBDV).

16 Claims, 1 Drawing Sheet

OTHER PUBLICATIONS

Snyder, D.B. et al. (1994). Molecular Epidemiology of Infectious Bursal Disease Virus in the United States. Proceedings of the International symposium on infectious bursal disease and chicken infectious anaemia, Rauischholzhausen, Germany. 60-70.

Snyder, D.B. et al. (1992). Naturally occurring-neutralizing monoclonal antibody escape variants define the epidemiology of infectious bursal disease viruses in the United States. Archives of Virology. 127:89-101.

Tsai, H.J. et al. (1992). Effect of Cell-Culture Passage on the Pathogenicity and Immunogenicity of Two Variant Strains of Infectious Bursal Disease Virus. Avian Diseases. 36:415-422.

Vakharia, V. et al. (1994). Molecular basis of antigenic variation in infectious bursal disease virus. Virus Research. 31:265-273.

van Loon, A.A.W.M. et al. (1994). Rapid Quantification of Infectious Bursal Disease (IBD) Challenge, Field or Vaccine Virus Strains. Proceedings of the International symposium on infectious bursal disease and chicken infectious anaemia, Rauischholzhausen, Germany. 179-187.

van Loon, A.A.W.M. et al. (2002). Alteration of amino acids in VP2 of very virulent infectious bursal disease virus results in tissue culture adaptation and attenuation in chickens. Journal of General Virology. 83:121-129.

Wang, M.-Y. et al. (2000). Self-Assembly of the Infectious Bursal Disease Virus Capsid Protein, rVP2, Expressed in Insect Cells and Purification of Immunogenic Chimeric rVP2H Particles by Immobilized Metal-Ion Affinity Chromatography. Biotechnology and Bioengineering. 67(1):104-111.

Wang, M.-Y. et al. Database EMBL 'Online! (Jul. 20, 1999). Expression, Purification, and Protection of the Recombinant Infectious bursal disease virus structural protein (VP2) produced by insect cells. Database EMBL 'Online! AF109154.

Yao, K. et al. (1998). Generation of a Mutant Infectious Bursal Disease Virus That Does Not Cause Bursal Lesions. Journal of Virology. 72(4), 2647-2654.

Ho, J.Y. et al. (1999). Expression, purification, and characterization of the infectious bursal disease virus -like particles produced by insect cells. Journal of the Chinese Chemical Society. 46:5 pp. 743-750. Publisher: Chinese Chemical Society. ISSN: 0009-4536.

* cited by examiner

Growth Kinetics in Cell Culture

TCID50/ml

- D78A
- PS-D78A
- Mut1
- PS-Mut1
- Mut2
- PS-Mut2
- Mut10
- Mut11 h p.i.

Group 1: D78A ; Mut1; Mut2:              63+, 69+, 57-, 67-

Group 2: PS-D78A ; PS-Mut1; PS-Mut2:     63+, 69+, 57-, 67+

Group 3: Mut10 ; Mut11:                  63-, 69+, 57+, 67-

SEQUENCE LISTING

```
<160> NUMBER OF SEQ ID NOS: 37

<210> SEQ ID NO 1
<211> LENGTH: 6
<212> TYPE: PRT
<213> ORGANISM: Artificial
<220> FEATURE:
<223> OTHER INFORMATION: Mutant of classic IBDV

<400> SEQUENCE: 1

Gly Gly Gln Ala Gly Asp
1               5

<210> SEQ ID NO 2
<211> LENGTH: 6
<212> TYPE: PRT
<213> ORGANISM: Artificial
<220> FEATURE:
<223> OTHER INFORMATION: Mutant of classic IBDV

<400> SEQUENCE: 2

Gly Gly Gln Ala Gly Glu
1               5

<210> SEQ ID NO 3
```

-continued

```
<211> LENGTH: 6
<212> TYPE: PRT
<213> ORGANISM: Artificial
<220> FEATURE:
<223> OTHER INFORMATION: Mutant of classic IBDV

<400> SEQUENCE: 3

Asp Gly Gln Ala Gly Asp
1               5

<210> SEQ ID NO 4
<211> LENGTH: 6
<212> TYPE: PRT
<213> ORGANISM: Artificial
<220> FEATURE:
<223> OTHER INFORMATION: Mutant of classic IBDV

<400> SEQUENCE: 4

Asp Gly Gln Ala Gly Glu
1               5

<210> SEQ ID NO 5
<211> LENGTH: 6
<212> TYPE: PRT
<213> ORGANISM: Artificial
<220> FEATURE:
<223> OTHER INFORMATION: Mutant of classic IBDV

<400> SEQUENCE: 5

Asn Gly Gln Ala Gly Glu
1               5

<210> SEQ ID NO 6
<211> LENGTH: 6
<212> TYPE: PRT
<213> ORGANISM: Artificial
<220> FEATURE:
<223> OTHER INFORMATION: Mutant of classic IBDV

<400> SEQUENCE: 6

Gly Gly Gln Glu Gly Asp
1               5

<210> SEQ ID NO 7
<211> LENGTH: 6
<212> TYPE: PRT
<213> ORGANISM: Artificial
<220> FEATURE:
<223> OTHER INFORMATION: Mutant of classic IBDV

<400> SEQUENCE: 7

Asp Gly Gln Glu Gly Asp
1               5

<210> SEQ ID NO 8
<211> LENGTH: 6
<212> TYPE: PRT
<213> ORGANISM: Artificial
<220> FEATURE:
<223> OTHER INFORMATION: Mutant of classic IBDV

<400> SEQUENCE: 8

Asn Gly Gln Glu Gly Asp
1               5

<210> SEQ ID NO 9
<211> LENGTH: 6
```

```
<212> TYPE: PRT
<213> ORGANISM: Artificial
<220> FEATURE:
<223> OTHER INFORMATION: Mutant of classic IBDV

<400> SEQUENCE: 9

Asn Gly Gln Glu Gly Glu
1               5

<210> SEQ ID NO 10
<211> LENGTH: 6
<212> TYPE: PRT
<213> ORGANISM: Artificial
<220> FEATURE:
<223> OTHER INFORMATION: Mutant of classic IBDV

<400> SEQUENCE: 10

Gly Gly Gln Ala Gly Asp
1               5

<210> SEQ ID NO 11
<211> LENGTH: 6
<212> TYPE: PRT
<213> ORGANISM: Artificial
<220> FEATURE:
<223> OTHER INFORMATION: Mutant of classic IBDV

<400> SEQUENCE: 11

Gly Gly Gln Ala Gly Glu
1               5

<210> SEQ ID NO 12
<211> LENGTH: 6
<212> TYPE: PRT
<213> ORGANISM: Artificial
<220> FEATURE:
<223> OTHER INFORMATION: Mutant of classic IBDV

<400> SEQUENCE: 12

Asp Gly Gln Ala Gly Asp
1               5

<210> SEQ ID NO 13
<211> LENGTH: 6
<212> TYPE: PRT
<213> ORGANISM: Artificial
<220> FEATURE:
<223> OTHER INFORMATION: mutant of pD78A

<400> SEQUENCE: 13

Asp Gly Gln Ala Gly Glu
1               5

<210> SEQ ID NO 14
<211> LENGTH: 6
<212> TYPE: PRT
<213> ORGANISM: Artificial
<220> FEATURE:
<223> OTHER INFORMATION: Mutant of classic IBDV

<400> SEQUENCE: 14

Asp Gly Gln Glu Gly Asp
1               5

<210> SEQ ID NO 15
<211> LENGTH: 6
<212> TYPE: PRT
```

```
<213> ORGANISM: Artificial
<220> FEATURE:
<223> OTHER INFORMATION: Mutant of classic IBDV

<400> SEQUENCE: 15

Asn Gly Gln Ala Gly Asp
1               5

<210> SEQ ID NO 16
<211> LENGTH: 6
<212> TYPE: PRT
<213> ORGANISM: Artificial
<220> FEATURE:
<223> OTHER INFORMATION: Mutant of classic IBDV

<400> SEQUENCE: 16

Asn Gly Gln Ala Gly Glu
1               5

<210> SEQ ID NO 17
<211> LENGTH: 6
<212> TYPE: PRT
<213> ORGANISM: Artificial
<220> FEATURE:
<223> OTHER INFORMATION: Mutant of classic IBDV

<400> SEQUENCE: 17

Asn Gly Gln Glu Gly Asp
1               5

<210> SEQ ID NO 18
<211> LENGTH: 6
<212> TYPE: PRT
<213> ORGANISM: Artificial
<220> FEATURE:
<223> OTHER INFORMATION: Mutant of classic IBDV

<400> SEQUENCE: 18

Asn Gly Gln Glu Gly Glu
1               5

<210> SEQ ID NO 19
<211> LENGTH: 31
<212> TYPE: PRT
<213> ORGANISM: Infectious bursal disease virus

<400> SEQUENCE: 19

Ser Asp Arg Pro Arg Val Tyr Thr Ile Thr Ala Ala Asp Asp Tyr Gln
1               5                   10                  15

Phe Ser Ser Gln Tyr Gln Pro Gly Gly Val Thr Ile Thr Leu Phe
            20                  25                  30

<210> SEQ ID NO 20
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 20
gaccatgaca tctgatcccc tgcctgaccg tcacttttgg aggtc                45

<210> SEQ ID NO 21
<211> LENGTH: 45
<212> TYPE: DNA
<213> ORGANISM: Artificial
```

<210> SEQ ID NO 22
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 21
gaccatgaca tctgttcccc tgcctgaccg tcacttttgg aggtc    45

<210> SEQ ID NO 22
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 22
gaccatgaca tctgatcccc ttcctgaccg tcacttttgg aggtc    45

<210> SEQ ID NO 23
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 23
gaccatgaca tctgttcccc ttcctgaccg tcacttttgg aggtc    45

<210> SEQ ID NO 24
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 24
gaccatgaca tctgttcccc tgcctgacca ccacttttgg aggtc    45

<210> SEQ ID NO 25
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 25
gaccatgaca tctgatcccc ttcctgacca ccacttttgg aggtc    45

<210> SEQ ID NO 26
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 26
gaccatgaca tctgttcccc ttcctgacca ccacttttgg aggtc    45

<210> SEQ ID NO 27
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 27
gaccatgaca tctgatcccc tgcctgaccg ttacttttgg aggtc    45

<210> SEQ ID NO 28
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 28
gaccatgaca tctgttcccc tgcctgaccg ttactttttgg aggtc         45

<210> SEQ ID NO 29
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 29
gaccatgaca tctgatcccc ttcctgaccg ttactttttgg aggtc         45

<210> SEQ ID NO 30
<211> LENGTH: 45
<212> TYPE: DNA
<213> ORGANISM: Artificial
<220> FEATURE:
<223> OTHER INFORMATION: oligonucleotide for site-directed mutagenesis

<400> SEQUENCE: 30
gaccatgaca tctgttcccc ttcctgaccg ttactttttgg aggtc         45

<210> SEQ ID NO 31
<211> LENGTH: 39
<212> TYPE: DNA
<213> ORGANISM: Artificial
<220> FEATURE:
<223> OTHER INFORMATION: oligonucleotide for site-directed mutagenesis

<400> SEQUENCE: 31
attgttaccc caccggtttg gtactgtgat gagaattgg         39

<210> SEQ ID NO 32
<211> LENGTH: 30
<212> TYPE: DNA
<213> ORGANISM: Artificial
<220> FEATURE:
<223> OTHER INFORMATION: oligonucleotide for site-directed mutagenesis

<400> SEQUENCE: 32
gattgttacc ccaccgcttt ggtactgtga         30

<210> SEQ ID NO 33
<211> LENGTH: 36
<212> TYPE: DNA
<213> ORGANISM: Artificial
<220> FEATURE:
<223> OTHER INFORMATION: oligonucleotide for site-directed mutagenesis

<400> SEQUENCE: 33
gtcactgcta ggctcccaga tgccgaccat gacatc         36

<210> SEQ ID NO 34
<211> LENGTH: 6
<212> TYPE: PRT
<213> ORGANISM: Artificial
<220> FEATURE:
<223> OTHER INFORMATION: Mutant of classic IBDV

<400> SEQUENCE: 34

Asp Gly Gln Glu Gly Glu
1               5

<210> SEQ ID NO 35
<211> LENGTH: 6
<212> TYPE: PRT
<213> ORGANISM: Artificial
<220> FEATURE:
<223> OTHER INFORMATION: Mutant of classic IBDV

<400> SEQUENCE: 35

Gly Gly Gln Glu Gly Glu
1               5

<210> SEQ ID NO 36
<211> LENGTH: 575
<212> TYPE: DNA
<213> ORGANISM: Infectious bursal disease virus
<220> FEATURE:
<221> NAME/KEY: CDS
<222> LOCATION: (1)..(573)
<220> FEATURE:
<223> OTHER INFORMATION: VP2

<400> SEQUENCE: 36

```
gtc ctc agc tta ccc aca tca tat gat ctt ggg tat gtg agg ctt ggt      48
Val Leu Ser Leu Pro Thr Ser Tyr Asp Leu Gly Tyr Val Arg Leu Gly
1               5                   10                  15 gac ccc att cct gct ata ggg ctt gac cca aaa atg gta gcc aca tgt      96
Asp Pro Ile Pro Ala Ile Gly Leu Asp Pro Lys Met Val Ala Thr Cys
            20                  25                  30 gac agc agt gac agg ccc aga gtc tac acc ata act gca gcc gat gat     144
Asp Ser Ser Asp Arg Pro Arg Val Tyr Thr Ile Thr Ala Ala Asp Asp
        35                  40                  45 tac caa ttc tca tca cag tac caa tca ggt ggg gta aca atc aca ctg     192
Tyr Gln Phe Ser Ser Gln Tyr Gln Ser Gly Gly Val Thr Ile Thr Leu
    50                  55                  60 ttc tca gcc aac att gat gct atc aca agc ctc agc att ggg gga gag     240
Phe Ser Ala Asn Ile Asp Ala Ile Thr Ser Leu Ser Ile Gly Gly Glu
65                  70                  75                  80 ctc gtg ttc cat aca agc gtc caa ggc ctt gca ctg aac gcc acc atc     288
Leu Val Phe His Thr Ser Val Gln Gly Leu Ala Leu Asn Ala Thr Ile
                85                  90                  95 tac ctt ata ggc ttt gat ggg act aca gta atc acc aga gct gtg gcc     336
Tyr Leu Ile Gly Phe Asp Gly Thr Thr Val Ile Thr Arg Ala Val Ala
            100                 105                 110 tca gac aat ggg ctg act acc ggc atc gac aat ctt atg cca ttc aat     384
Ser Asp Asn Gly Leu Thr Thr Gly Ile Asp Asn Leu Met Pro Phe Asn
        115                 120                 125 ctt gtg att cca acc aac gag ata acc cag cca atc aca tcc atc aaa     432
Leu Val Ile Pro Thr Asn Glu Ile Thr Gln Pro Ile Thr Ser Ile Lys
    130                 135                 140 ctg gag ata gtg acc tcc aaa agt ggc ggt cag gca ggg gac cag atg     480
Leu Glu Ile Val Thr Ser Lys Ser Gly Gly Gln Ala Gly Asp Gln Met
145                 150                 155                 160 tca tgg tcg gca agt ggg agc cta gca gtg aca atc cat ggt ggc aac     528
Ser Trp Ser Ala Ser Gly Ser Leu Ala Val Thr Ile His Gly Gly Asn
                165                 170                 175 tat cca ggg gcc ctc cgt ccc gtc aca cta gta gcc tac gaa aga gt      575
Tyr Pro Gly Ala Leu Arg Pro Val Thr Leu Val Ala Tyr Glu Arg
            180                 185                 190
```

```
<210> SEQ ID NO 37
<211> LENGTH: 191
<212> TYPE: PRT
<213> ORGANISM: Infectious bursal disease virus

<400> SEQUENCE: 37

Val Leu Ser Leu Pro Thr Ser Tyr Asp Leu Gly Tyr Val Arg Leu Gly
 1               5                  10                  15

Asp Pro Ile Pro Ala Ile Gly Leu Asp Pro Lys Met Val Ala Thr Cys
                20                  25                  30

Asp Ser Ser Asp Arg Pro Arg Val Tyr Thr Ile Thr Ala Ala Asp Asp
            35                  40                  45

Tyr Gln Phe Ser Ser Gln Tyr Gln Ser Gly Gly Val Thr Ile Thr Leu
        50                  55                  60

Phe Ser Ala Asn Ile Asp Ala Ile Thr Ser Leu Ser Ile Gly Gly Glu
65                  70                  75                  80

Leu Val Phe His Thr Ser Val Gln Gly Leu Ala Leu Asn Ala Thr Ile
                85                  90                  95

Tyr Leu Ile Gly Phe Asp Gly Thr Thr Val Ile Thr Arg Ala Val Ala
                100                 105                 110

Ser Asp Asn Gly Leu Thr Thr Gly Ile Asp Asn Leu Met Pro Phe Asn
            115                 120                 125

Leu Val Ile Pro Thr Asn Glu Ile Thr Gln Pro Ile Thr Ser Ile Lys
        130                 135                 140

Leu Glu Ile Val Thr Ser Lys Ser Gly Gly Gln Ala Gly Asp Gln Met
145                 150                 155                 160

Ser Trp Ser Ala Ser Gly Ser Leu Ala Val Thr Ile His Gly Gly Asn
                165                 170                 175

Tyr Pro Gly Ala Leu Arg Pro Val Thr Leu Val Ala Tyr Glu Arg
                180                 185                 190
```

INFECTIOUS BURSAL DISEASE VIRUS (IBDV) MUTANT EXPRESSING VIRUS NEUTRALISING EPITOPES SPECIFIC FOR CLASSIC-AND VARIANT IBDV STRAINS

The present invention is concerned with a classic infectious bursal disease virus (IBDV) mutant and a vaccine comprising such a classic IBDV mutant.

BACKGROUND OF THE INVENTION

Infectious bursal disease virus (IBDV) is a member of the Birnaviridae family. Viruses in this family have a very similar genomic organisation and a similar replication cycle. The genomes of these viruses consist of two segments (A and B) of double-stranded (ds) RNA. The larger segment A encodes a polyprotein, which is cleaved by autoproteolysis to form mature viral proteins VP2, VP3 and VP4. VP2 and VP3 are the major structural proteins of the virion. VP2 is the major host-protective immunogen of birnaviruses, and contains the immunogenic regions responsible for the induction of virus neutralising antibodies.

For IBDV, two serotypes exist, serotype 1 and 2. The two serotypes can be differentiated by virus neutralisation (VN) tests. Serotype 1 viruses have been shown to be pathogenic to chickens, while serotype 2 IBDV only causes sub-acute disease in turkeys. Infectious Bursal disease (IBD), also called Gumboro disease, is an acute, highly-contagious viral infection in chickens that has lymphoid tissue as its primary target with a selective tropism for cells of the bursa of Fabricius. The morbidity rate in susceptible flocks is high, with rapid weight loss and moderate to high mortality rates. Chicks that recover from the disease may have immune deficiencies because of the destruction of the bursa of Fabricius, which is essential to the defense mechanism of the chicken. The IBD-virus causes severe immunosuppression in chickens younger than 3 weeks of age and induces bursal lesions in chicks up to 3 months old.

For many years the disease could be prevented by inducing high levels of antibodies in breeder flocks by the application of an inactivated vaccine, to chickens that had been primed with attenuated live IBDV vaccine. This has kept economic losses caused by IBD to a minimum. Maternal antibodies in chickens derived from vaccinated breeders prevent early infection with IBDV and diminish problems associated with immunosuppression. In addition, attenuated live vaccines have also been used successfully in commercial chicken flocks after maternal antibodies had declined.

Historically, IBD viruses consisted of only one type that is known as "classic" IBD virus. However, in the mid-1980s acute disease in flocks vaccinated with vaccines based on classic IBDV was observed, in particular in the US. It was found that this disease was caused by IBD viruses that had a different immunogenic make-up. These new viruses probably emerged as a result of genetic drift. The emergence of these so-called "variant" IBDV strains required the design of new IBD vaccination programmes, because the classic IBDV vaccine strains could not induce an adequate cross-protection. The most important variant subtypes of serotype 1 IBDVs identified in the past were the Delaware-E, GLS, RS/593 and DS326 variants. The variant strains can be identified and distinguished from classic strains by a virus neutralisation test, a panel of monoclonal antibodies or RT-PCR.

Delaware variant-E was reported by Rosenberger et al. (Proc. 20th Natl. Meet. on Poultry Health and Condemnations; Ocean City, Md., USA, 94-101, 1985) and Snyder et al. (Avian Diseases 32, 535-539, 1985). GLS virus was isolated in the USA in 1987 and DS326 (GLS-like) was isolated in the USA in 1988 (Snyder et al., Arch. Virol. 127, 89-101, 1992 and van Loon et al. Proceedings of the International symposium on infectious bursal disease and chicken infectious anaemia, Rauischholzhausen, Germany, 179-187, 1994). Strain RS/593 (variant-E like) was also isolated in the USA, in 1993 (Snyder, et al. Proceedings of the International symposium on infectious bursal disease and chicken infectious anaemia, Rauischholzhausen, Germany, 65-70, 1994).

A panel of virus neutralising monoclonal antibodies (moab) is commonly used in the art in an antigen-capture enzyme immuno assay (AC-ELISA) to identify the various IBDV types. The reactivity pattern of these moabs with the existing IBDV strains is summarized in Table 1 below.

TABLE 1

The different variant IBDV strains as determined by the moab panel pattern

| Strain | Moab | | | | | | | | |
|---|---|---|---|---|---|---|---|---|---|
| | 8 | B69 | R63 | 10 | BK9 | 67 | 57 | 44A1 | 179 |
| Classic | + | + | + | + | − | − | − | + | + |
| Delaware variant (-E) | + | − | + | − | + | + | − | + | + |
| RS/593 | + | − | − | − | − | + | − | − | + |
| GLS | + | − | − | + | − | − | + | + | + |
| DS326 | + | − | − | + | − | − | + | + | − |

VN moabs R63 and B69 neutralise classic IBDV strains to high titres and moab B69 specifically binds to classic strains. moab BK9 uniquely binds to Delaware variant-E strains. A positive reaction by moab 57 can be used to separate the GLS- and DS326 strains from classic- and Delaware variant strains. These and other moabs are generally used in the field to distinguish between IBDV (variant) strains by determining the reaction pattern of the panel of available moabs. The hybridomas secreting the moabs are also available from the ATCC (Rockville, USA) under the following accession numbers: R63 (HB-9490), 8 (HB-10174), B29 (HB-9746), BK-9 (HB-10157), 67 (HB-11122), 57 (HB-10156), B69 (HB-9437) and 179 (HB-10158). Variant IBDV strains and hybridomas are also available from the Collection Nationale de Cultures de Microorganismes of the Institute Pasteur, Paris, France under the following accession no.'s: DS 326 (I-910), GLS (I-792 and I-793) and moab 10 (I-2812).

Although the importance of some regions and distinct amino acids within the VP2 protein of IBDV for the antigenic variation between IBDV strains has been proposed (Vakharia et al., Virus Research 31, 265-273, 1994 and Snyder et al., Avian Diseases 38, 701-707, 1994), the mandatory presence of all the amino acids for the formation of IBDV neutralising epitopes has not been determined yet. In Virus Research 49, 131-137, 1997, Vakharia et al. reported that amino acid proline is present in variant E IBDV. In international patent application WO 95/26196 Vakharia et al. suggested the involvement of amino acids 286 (Ile), 318(Asp) and 323 (Glu) in the context of the binding of a variant E VP2 protein with moab 67. In addition, multiple amino acid sequence differences between VP2 proteins of classic- and variant VP2 IBDV are disclosed. Amino acid positions 222 (Pro), 249 (Gln) and 254 (Gly) were considered relevant for the formation of the B69 epitope in a GLS VP2 protein.

EP 1170302 (Akzo Nobel N.V.) discloses the preparation of a variant E IBDV mutant with improved immunogenicty against classic IBDV strains. This IBDV mutant was obtained by introducing mutations in the variant E VP2 coding region in the codons for the amino acids 253 (Gln to His), 284 (Ala to Thr) and 254 (Ser to Gly), 270 (Ala to Thr). None of these variant E IBDV mutants express a VP2 protein that binds with moab B69.

However, no information is disclosed therein that allows the generation of a classic IBDV mutant that also expresses a variant E virus neutralising epitope. Such a mutant would be very useful in vaccines to induce protection against disease caused by both classic- and variant IBDV strains in the field.

In the present invention a new IBDV mutant has been constructed based on a classic IBDV by introducing mutations in the VP2 coding region such that the VP2 protein expressed by the virus comprises virus neutralising epitope 67 that is typical for variant IBDVs. The inventors found that in the context of a classic VP2 protein the reactivity with moab 67 is influenced by amino acid sequences located about 100 amino acids apart. Furthermore, the assumption made by Vakharia et al. that 286 (Ile), 318(Asp) and 323 (Glu) influence the presence of the 67 epitope is not correct. In fact the inventors have found that the emergence of the 67 epitope in the context of a classic IBDV VP2 protein depends on the exchange of proline at position 222 to serine or threonine and on the presence of certain amino acid sequences in positions 318-322. The exchange of proline to serine or threonine at position 222 in the presence of the amino acid sequences naturally present in a classic IBDV VP2 protein at positions 318-323 (Gly-Gly-Gln-Ala-Gly-Asp) (SEQ ID NO:1) lead to the emergence of the 67 epitope in a classic IBDV VP2 protein.

SUMMARY OF THE INVENTION

Therefore, the present invention provides a classic infectious bursal disease virus mutant that expresses a VP2 protein that binds with monoclonal antibody (moab) B69, characterised in that the VP2 protein also binds with moab 67, secreted by hybridoma cell lines HB-9437 and HB-11122, deposited at the ATCC, Rockville, USA, respectively.

BRIEF DESCRIPTION OF THE FIGURES

FIG. 1 illustrates the growth kinetics of various IBDV having amino acid exchange Mutations.

DETAILED DESCRIPTION OF THE EMBODIMENTS

The IBDV VP2 protein consists of 512 amino acids and is located on the polyprotein at amino acid positions 1-512. The nucleotide sequences of (the complete segment A comprising) the VP2 coding region and the corresponding amino acid sequences of the VP2 protein of many classic IBDV strains have been determined (U.S. Pat. No. 5,871,744, EP 887,412 for D78; NCBI GeneBank)

All known moabs showing virus neutralising properties, including moab B69 that is specific for classic IBDV strains, are exclusively raised against the VP2 protein and recognise conformational-dependent epitopes. Comparison of many classic- and variant VP2 amino acid sequences, in particular of variant E and GLS, are disclosed in Vakharia et al. (1994, supra) and Heine et al. (J. Gen. Virol. 72, 1835-1843, 1991). Although biological variation among virus strains exist, within the classic type of IBDV strains the amino acid sequence of the VP2 protein is strongly conserved. Amino acid homology between classic VP2 amino acid sequences varies between 98%-99.4% over the full length of the protein (based on a comparison with the VP2 amino acid sequence of IBDV strain D78). A central region within the VP2 protein was identified which contains the most variable part of VP2. This region is located at amino acid positions 206 to 350 (Bayliss et al., J. Gen. Virol. 71, 1303-1312, 1987) and amino acid homology between classic VP2 amino acid sequences within this region varies between 95.9%-97.9% (based on a comparison with the VP2 amino acid sequence of IBDV strain D78). Within this central region two hypervariable regions are identified, at positions 212-224 and 314-326, in which most of the amino acid changes between different types of IBDV strains occur (Vakharia et al., 1994, supra). Despite this, most classic IBDV strains comprise an amino acid sequence in the region 200-230 that is identical to that in VP2 of IBDV strain D78: Ser-Asp-Arg-Pro-Arg-Val-Tyr-Thr-Ile-Thr-Ala-Ala-Asp-Asp-Tyr-Gln-Phe-Ser-Ser-Gln-Tyr-Gln-Pro-Gly-Gly-Val-Thr-Ile-Thr-Leu-Phe (SEQ ID no. 19). Sequences are analyzed herein with the Wisconsin Package, version 8 (Genetics Computer Group, Madison, Wis.)

Therefore, a classic IBDV is defined herein as an isolated IBDV comprising a VP2 coding region that expresses a VP2 protein that is able to bind with moab B69.

More in particular, a classic IBDV is defined as an isolated IBDV that comprises a VP2 amino acid sequence at positions 200-230 that is the same as that of strain D78 (SEQ ID no. 19).

The reaction of a moab with an IBDV can be determined by means of an AC-ELISA that is commonly used in the art for this purpose, such as described by Snyder et al. (1992, supra) and van der Marel et al. (Dtsch. Tierartzl. Wschr. 97, 81-83, 1990).

Alternatively, the reaction of an IBDV with a moab can also be determined by means of an immunofluoresence assay as described in the Example 1.

A classic IBDV mutant according to the invention was also isolated from diseased animals in a flock that was vaccinated with a classic IBDV vaccine. This new variant IBDV isolated from nature is antigenically different from the known classic- and variant IBDVs as demonstrated by its moab binding pattern (Example 3). Table 6 shows that the IBDV mutant binds with moab B69 (that usually binds with classical IBDV) and moab 67 (that usually binds with variant E IBDV).

A preferred classical IBDV mutant according to the invention expresses a VP2 protein that in addition to moab B69 and moab 67 binds with moab R63, secreted by hybridoma cell line HB-9490, deposited at the ATCC, Rockville, USA. The moab R63 is able to neutralise both classic- and variant E strains of IBDV.

The present invention for the first time identifies which amino acid residues in the context of a classic VP2 protein are required and sufficient for (i) the formation of a neutralising epitope that binds with moab R63 (classic and variant E), (ii) the additional formation of a neutralising epitope that binds with moab 67 (variant E) and (iii) for the additional formation of a neutralising epitope that binds with moab 57 (GLS).

The inventors prepared a number of the IBDV mutants as defined above by introducing mutations in the VP2 coding region of a classic IBDV strain (Example 1). The results obtained demonstrate that identical epitopes can be folded by different amino acid sequences, whereas other amino acid sequences fail to generate the variant epitopes. Therefore, a specific coding capacity exists for a specific epitope. A summary of the relevant amino acid sequences that are required for the appropriate folding of the 67, 57 and R63 epitopes is presented in Table 2 (SEQ ID No.'s 1-5, 6-9 and 10-18, respectively). The information provided in Table 2 allows the skilled person to generate classic IBDV mutants capable of expressing a VP2 protein that in addition to virus neutralising epitope B69 also comprises virus neutralising epitope 67 that is specific for variant E IBDV strains.

TABLE 2

Summary of amino acids essential for epitope folding

| Epitope | aa 222 | aa 318 | aa 319 | aa 320 | aa 321 | aa 322 | aa 323 | aa 330 | SEQ ID no. (318-323) |
|---|---|---|---|---|---|---|---|---|---|
| 67  | S or T    | G | G | Q | A | G | D | R or S | 1 |
| 67  | S or T    | G | G | Q | A | G | E | R or S | 2 |
| 67  | S or T    | D | G | Q | A | G | D | R or S | 3 |
| 67  | S or T    | D | G | Q | A | G | E | R or S | 4 |
| 67  | S or T    | N | G | Q | A | G | E | R or S | 5 |
| 57  | P, S or T | G | G | Q | E | G | D | R or S | 6 |
| 57  | P, S or T | D | G | Q | E | G | D | R      | 7 |
| 57  | P, S or T | N | G | Q | E | G | D | R      | 8 |
| 57  | P, S or T | N | G | Q | E | G | E | R      | 9 |
| R63 | P, S or T | G | G | Q | A | G | D | R or S | 10 |
| R63 | P, S or T | G | G | Q | A | G | E | R or S | 11 |
| R63 | P, S or T | D | G | Q | A | G | D | R or S | 12 |
| R63 | P, S or T | D | G | Q | A | G | E | R or S | 13 |
| R63 | P, S or T | D | G | Q | E | G | D | S      | 14 |
| R63 | P, S or T | N | G | Q | A | G | D | R or S | 15 |
| R63 | P, S or T | N | G | Q | A | G | E | R or S | 16 |
| R63 | P, S or T | N | G | Q | E | G | D | S      | 17 |
| R63 | P, S or T | N | G | Q | E | G | E | S      | 18 |

Therefore, a particularly preferred classic IBDV mutant is a mutant that binds with moab B69 and moab 67, and comprises one or more mutations in a classical VP2 coding region, such that the coding region comprises, (i) a codon for the amino acid at position 222 encoding serine or threonine, and (ii) a nucleotide sequence encoding an amino acid sequence shown in any of the SEQ ID. no. 1-5 at positions 318-323.

It was found that the amino acid sequence at positions 318-323 as shown in Table 2 resulted in a proper folding of the 67 epitope only in case the amino acid at position 222 (proline) was changed to serine or threonine, implying that proper folding of the epitope is influenced by amino acids located 100 positions apart.

Although the amino acid at position 330 is not critical, an advantageous IBDV mutant further comprises a codon encoding the amino acid arginine or serine at this position.

A further advantageous property of a classic IBDV mutant as defined above is that such a mutant also expresses a VP2 protein having the required amino acid sequence for the proper folding of the R63 virus neutralising epitope. It is demonstrated in the Table 2 and Example 1 that an IBDV that expresses a VP2 protein having an amino acid sequence at positions 318-323 as shown in any of the SEQ ID no. 14-15 and 17-18 (in addition to an serine or threonine at position 222) displays epitope R63 but fails to display epitope 67.

A further surprising observation made by the inventors is that an exchange of an amino acid in the VP2 coding region at positions 318-323 of a classic IBDV strain results in a decrease of the growth properties of such mutants. Such mutants display an attenuated phenotype for chickens and can advantageously be used as vaccine candidates with improved safety properties, in particular in vaccines that are administered via the in ovo route. Therefore, the present invention also provides a classic IBDV mutant that comprises one or more mutations in a classic VP2 coding region, such that the coding region comprises a nucleotide sequence encoding an amino acid sequence at positions 318-323 that is different from the natural amino acid sequence Gly-Gly-Gln-Ala-Gly-Asp (SEQ ID no. 1). Preferably, these classic IBDV mutants comprise an amino acid sequence at these positions as shown in any of the SEQ ID No. 2-9 and 11-18, optionally, together with an amino acid at position 222 and/or 330 as defined above.

A classic IBDV mutant according to the invention can be prepared by introducing the required mutations in a VP2 coding region derived from any classic IBDV strain isolatable from the field or used in vaccines. Suitable IBDV strains include the well-known IBDV strains present in commercially available vaccines, such as D78, PBG98, 228E and 89-03 (Intervet Interntional B.V.). IBDV strain D78 (U.S. Pat. No. 4,530,831) is also available from the ATCC under accession no. VR-2041. The nucleotide sequence of the complete segment A of strain D78, including the VP2 coding region, and the amino acid sequence of the corresponding (poly) protein is disclosed in U.S. Pat. No. 5,871,744 and EP application 887,412.

In particular, a classic IBDV mutant is provided that comprises one or more mutations in a VP2 coding region of IBDV strain D78.

A further preferred classic IBDV mutant according to the present invention comprises the complete genetic backbone of the segment A of a classic IBDV strain, including the mutated classic VP2 coding region as described above. More in particular, a classic IBDV mutant as defined above is derived from IBDV strain D78.

However, a classic IBDV mutant according to the invention can also be based on the genetic backbone of a variant IBDV strain, such as a variant E or GLS strain. In such a "chimeric" classic IBDV mutant, the VP2 coding sequences on the genetic backbone of segment A of a variant IBDV strain are replaced by the corresponding, relevant classic VP2 coding sequences that additionally comprise the desired mutations that are responsible for the new variant epitopes on the classic IBDV mutant.

The generation of a classic IBDV mutant according to the invention can be achieved by means of the recently established infectious cRNA system for IBDV (Mundt and Vakharia, Proc. Natl. Acad. Sci. USA 93, 11131-11136, 1996). This reverse genetics system provides the possibility to introduce mutations in the RNA genome of the IBDV. The most important step in this reverse genetics system is to provide full length cDNA clones of the segments A and B of the IBDV, including the nucleotides of the 5'- and 3'-ends of both these segments. After cloning procedures, the full length sequences of segment A and B are operably linked to a promoter which is able to bind a DNA dependent RNA polymerase, such as the T7, SP6 or T3 polymerase, the T7 promoter being preferred. The DNA dependent polymerase is able to describe viral cRNA from full length cDNA clones of segment A and B, respectively. This cRNA is able to induce replication of the virus and the isolation of viable virus. This procedure can be performed with every natural occurring IBDV.

Reverse genetics systems have been described for various IBDV strains, such as D78 (Yao et al., J. Virol. 72, 2647-2657, 1998), strain HK46 (Lim et al., J. Virol. 73, 2854-2862, 1999), CEF 94 (Boot et al., Virology 265, 330-341, 1999) and UK661 (van Loon et al., J. Gen. Virol. 83, 121-129, 2002).

The desired mutations can be introduced into the IBDV genome by means of methods generally known in the art for this purpose. In particular, the mutation(s) are introduced by means of site-directed mutagenises. Methods for introducing a mutation in the IBDV genome are described herein, but are also generally used in the art (Mundt and Vakharia, 1996, supra; Yao et al., J. Virology 72, 2647-2654, 1998; Mundt et al., 1999, supra; EP patent application no. 1170302; Current Protocols in Molecular Biology, eds.: F. M. Ausubel et al., Wiley N.Y., 1995 edition, pages 8.5.1.-8.5.9. and Kunkel et al. in Methods in Enzymology vol. 154, 376-382, 1987).

The numbers used herein to indicate the amino acid positions refer to numbering of the amino acids in the IBDV polyprotein as commonly used in the art. The numbers indicating the nucleotide positions are based on the complete nucleotide sequence of the segment A of the IBDV genome as described by Mundt and Müller (J. Gen. Virol. 77, 437-443, 1995; NCBI accession number X 84034).

The segment B of a classic IBDV mutant according to the invention can be derived from any IBDV strain, preferably from a classic IBDV strain, most preferably from strain D78 or P2 (U.S. Pat. No. 5,871,744 and EP patent application no. 887412).

As demonstrated in the Examples, the classic IBDV mutant according to the invention displays an immunogenic make-up that is not observed before for classic IBDV strains. The new classic IBDV mutant may form the basis of a new type of IBDV vaccine that can effectively protect poultry against disease conditions resulting from the infection by both classic- and variant IBDV strains. Therefore, another aspect of this invention is a vaccine for use in the protection of poultry against disease caused by IBDV infection, characterised in that the vaccine comprises a classical IBDV mutant as defined above, together with a pharmaceutical acceptable carrier or diluent.

The classical IBDV mutant can be incorporated into the vaccine as live attenuated or inactivated virus.

A vaccine according to the invention can be prepared by conventional methods such as for example commonly used for the commercially available live- and inactivated IBDV vaccines. Briefly, a susceptible substrate is inoculated with a classical IBDV mutant according to the invention and propagated until the virus replicated to a desired infectious titre after which IBDV containing material is harvested, optionally inactivated, and mixed with a pharmaceutical acceptable carrier or diluent.

Every substrate which is able to support the replication of IBDVs can be used to prepare a vaccine according to the present invention, including primary (avian) cell cultures, such as chicken embryo fibroblast cells (CEF) or chicken embryo liver cells (CEL), mammalian cell lines such as the VERO cell line or the BGM-70 cell line, or avian cell lines such as QT-35, QM-7 or LMH. Usually, after inoculation of the cells, the virus is propagated for 3-14 days, after which the cell culture supernatant is harvested, and if desired filtered or centrifuged in order to remove cell debris.

The classical IBDV mutant can also be propagated in embryonated chicken eggs.

If desired, attenuation of the classical IBDV can be obtained by standard serial passaging of the virus in cell cultures, for example in the primary cell cultures or established cell lines mentioned above (Bayyari et al., Avian Diseases 40, 516-532, 1996; Tsai et al., Avian diseases 36, 415-422, 1992).

Alternatively, the classical IBDV can be propagated in vivo in infected chickens followed by the isolation of the bursa of Fabricius from these infected animals, mixing it with diluent and homogenizing the mixture. IBDV propagated in this way commonly forms the basis of an inactivated vaccine.

The vaccine according to the invention containing the live virus can be prepared and marketed in the form of a suspension or in a lyophilised form and additionally contains a pharmaceutically acceptable carrier or diluent customary used for such compositions. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are the same as mentioned below.

Although administration by injection, e.g. intramuscularly, subcutaneously or in ovo of the live vaccine according to the present invention is possible, the vaccine is preferably administered by an inexpensive mass application route commonly used for IBDV vaccination. For IBDV vaccination this route includes drinking water, spray and aerosol vaccination.

Alternatively, the present invention provides a vaccine comprising the variant IBDV in an inactivated (killed) form. An advantage of an inactivated IBDV vaccine is the high levels of protective antibodies of long duration that can be obtained.

The aim of inactivation of the viruses harvested after the propagation step is to eliminate reproduction of the viruses. In general, this can be achieved by chemical or physical means well known in the art.

A vaccine containing the inactivated variant IBDV can, for example, comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

The vaccine according to the invention comprises an effective dosage of the classical IBDV mutant as the active component, i.e. an amount of immunising IBDV material that will induce immunity in the vaccinated birds against challenge by a virulent virus. Immunity is defined herein as the induction of a significant higher level of protection in a population of birds after vaccination compared to an unvaccinated group.

Typically, the live vaccine according to the invention can be administered in a dose of $10^0$-$10^9$ TCID$_{50}$ per animal, preferably in a dose ranging from $10^3$-$10^6$ TCID$_{50}$ per animal. Inactivated vaccines may contain the antigenic equivalent of $10^6$-$10^{10}$ TCID$_{50}$ per animal.

Inactivated vaccines are usually administered parenterally, e.g. intramuscularly or subcutaneously.

Although, the IBDV vaccine according to the present invention may be used effectively in chickens, also other poultry such as turkeys, guinea fowl and partridges may be successfully vaccinated with the vaccine. Chickens include broilers, pullets, reproduction stock and laying stock.

The age of the animals receiving a live or inactivated vaccine according to the invention is the same as that of the animals receiving the conventional live- or inactivated IBDV vaccines. For example, broilers (free of maternally derived antibodies-MDA) may be vaccinated at one-day-old or in ovo, whereas broilers with high levels of MDA are preferably vaccinated at 2-3 weeks of age. Laying stock or reproduction stock with low levels of MDA may be vaccinated at 1-10 days of age followed by booster vaccinations with inactivated vaccine on 6-12 and 16-20 weeks of age.

The invention also includes combination vaccines comprising, in addition to the classical IBDV mutant described above, one or more vaccine components of other pathogens infectious to poultry.

Preferably, the combination vaccine additionally comprises one or more vaccine strains of Mareks Disease virus (MDV), infectious bronchitis virus (IBV), Newcastle disease virus (NDV), egg drop syndrome (EDS) virus, turkey rhinotracheitis virus (TRTV) or reovirus.

EXAMPLES

Example 1

Preparation of Classic IBDV Mutants and Determination of Monoclonal Antibody Reactivity Material and Methods Generation of Mutated Segment A For site directed mutagenesis experiments pD78A (Mundt and Vakharia, supra, 1996; EP application 887412) was used. To this end pD78A was EcoRI/KpnI cleaved and the segment A containing fragment was ligated into appropriately cleaved pBlueScript KS+ to obtain pSK+-D78A. After preparation of single stranded DNA site directed experiments were performed according to Kunkel et al. (supra, 1987) using oligonucleotides as specified in Table 3. Oligonucleotides Mut 1, Mut 2, Mut3, Mut4, Mut5, Mut6, Mut7, Mut8, Mut9, Mut10, Mut11 were used to generate mutated plasmids pMut1, pMut2, pMut3, pMut4, pMut5, pMut6, pMut7, pMut8, pMut9, pMut10, and pMut11, respectively. Using this eleven mutated plasmids single stranded DNA was prepared and used together with single stranded DNA of pSK+-D78A in site directed mutagenisis experiments. These experiments were performed with one (P222S or R339S) or two oligonucleotides (P222S and R339S) in one experiment to obtain one or two exchanges of base triplets. Obtained mutagenised plasmids (shown in Table 4) were sequenced and used for further experiments.

Transfection of cRNA, Immunoflourescence Assays and Passaging of Generated Virus For in vitro transcription plasmids containing pD78A and mutagenised plasmids were linearized by cleavage with BsrG I. pP2B (Mundt & Vakharia, supra, 1996; EP application 887412) was linearized using Pst I. Further treatment of linearized DNA, transcription and transfection of RNA into BHK 21 cells were carried out as described by Mundt (J. Gen. Virol. 80, 2067-2076, 1999). For immunoflourescence assay BHK21 cells grown in 24 well tissue culture plates were transfected and 24 h after transfection aceton/methanol (50%/50%) fixed for 5 min and dried. Fixed cells were incubated with monoclonal antibodies 67, B69, 57, R63 and rabbit anti-IBDV serum (Mundt et al., J. Gen. Virol. 76, 437-443, 1995), respectively, diluted in phosphate buffered saline (PBS) for 30 min and rinsed trice with PBS. Cells were now incubated for 30 min in PBS diluted DTAF-conjugated goat anti-rabbit IgG or DTAF-conjugated goat anti-mouse IgG (Dianova, Hamburg, Germany) followed by three washes using PBS and one wash with destilled water. After air drying cells were mounted in 2.5% 1.4.-Diazobicyclo(2.2.2.)-octane (DABCO, Sigma, Deisenhofen, Germany) containing PBS with 90% glycerol. Fluorescence was visualised using a immerse fluorescence microscope.

For passaging of generated virus BHK21 cells grown in 6 well tissue culture plates were transfected in parallel to the transfection experiments in 24 well tissue culture plates and incubated for 24 h-48 h. After freeze/thaw at $-70°$ for at least one hour obtained supernatant was centrifuged at 6400×g for 10 min and passaged onto QM cells grown in 25 cm$^2$ tissue culture flask until CPE was visible. Supernatant was obtained as described above, aliquoted and stored at $-70°$ C. For analysis of viability and presence of reactivity with the mmAb QM-cells grown in 24 well tissue culture plates were infected with one aliqout and incubated for 24 h. Immunofluorescence assay was performed as described above.

Growth Analysis of Generated Virus in Cell Culture

To monitor growth CEC grown in 24 well tissue culture plate were infected with selected IBDV at a MOI of 1 for 1 h at 37° C. Thereafter, inoculum was removed, cells were washed with medium and 1 ml medium was added. Supernatants were harvested separately immediately thereafter (0 h), and after 8, 12, 16, 24 and 36 h of incubation at 37° C. and stored at $-70°$ C. Virus titers were obtained by determination of TCID50 using QM-cells (Quail muscle cells) grown in 96 well tissue culture plates. To this end supernatants were thawed and titrated in log10 steps. 100 µl each of the appropriate dilution was pipetted into four wells of a tissue culture plate followed by addition of 100 µl QM cells suspension ($10^6$ cells/ml). The plates were incubated at 37° C. After five days wells with CPE were couted as positive and TCID50 was determined following Spaerman (Brit. J. Psychol., 2, 227-242, 1908) and Karber (Arch. Exp. Path. Pharmak . . . , 162, 480-487, 1931). Average values and standard deviations of three independent experiments were calculated.

Results

Influence of the Exchange of Amino Acids in the Variable Region of VP2 on the Reactivity of Monoclonal Antibodies Amino acids located in the sequence of strain D78 at position 222 (proline), 318 (glycine), 321 (alanine), and 323 (aspartate) were exchanged to amino acids serine, threonine (P222S, P222T), aspartate, asparagine (G318D, G318N, glutamate (A321E), and glutamate (D323E), respectively, in different combinations (see Table 4). Exchange of proline in position 222 to serine resulted in an additional reactivity of moab 67 if the aa sequence of aa from position 318 to 323 was of following combinations: GGQAGD (SEQ ID NO: 10), DGQAGD (SEQ ID NO: 12), DGQAGE (SEQ ID NO: 13), GGQAGE (SEQ ID NO: 2), NGQAGE (SEQ ID NO: 5). The remaining combinations of the aa sequence from position 318 to 323 (DGQEGD (SEQ ID NO: 7), DGQEGE (SEQ ID NO: 34), GGQEGD (SEQ ID NO: 6), GGQEGE (SEQ ID NO:

35), NGQAGD (SEQ ID NO: 15), NGQEGD (SEQ ID NO: 8), NGQEGE (SEQ ID NO: 9)) seems to prevent the folding of the epitope characterized by moab 67 even if proline at position 222 was exchanged to serine. Binding of moab 57 was detected after exchange of aa 321 from alanine to glutamate independent if amino acid 222 (proline), 318 (glycine), and 323 (aspartate). But the exchange of arginine to serine at position 330 influenced the presence of the 57 epitope. Here if the performed exchange (R330S) was performed in presence of the combinations DGQEGD (SEQ ID NO: 7), NGQEGD (SEQ ID NO: 17), and NGQEGE (SEQ ID NO: 18), respectively, no reactivity with moab 57 was detected after co-tramsfection experiments. In contrast, the exchange R330S showed no influence on the reactivity with moab 57 in presence of the combination GGQEGD (SEQ ID NO: 6). The presence of reactivity of moab 57 and R63 excluded each other in the performed experiments since if the 57 epitope was present the R63 epitope was absent. Furthermore reactivity with moab R63 after co-transfection experiments was recorded after usage of plasmids encoding combinations GGQAGD (SEQ ID NO: 10), DGQAGD (SEQ ID NO: 12), DGQAGE (SEQ ID NO: 13), GGQAGE (SEQ ID NO: 2), NGQAGD (SEQ ID NO: 15), and NGQAGE (SEQ ID NO: 5) from aa 318 to 323 located in the VP2 region independent if aa 222 (proline) or aa 330 (argenine) was exchanged. Translated protein of cRNA of plasmids encoding the amino acid sequence DGQEGE (SEQ ID NO: 34) or GGQEGE (SEQ ID NO: 35) from position 318 to 323 of the polyprotein gene reacted only with the moab 69. Here also the exchange of aa 222 and/or 330 seems to have no influence on the reactivity. After all transfection experiments cells were freezed/thawed and the obtained supernatant was passaged. In each case viable virus was generated indicating that the performed mutagenised amino acids had no influence on viability and infectivity of cell culture of the virus.

Analysis of Growth in Cell Culture

To test if amino acid exchange influence the growth of mutated virus several mutated IBDV (D78, Mut1, Mut2, PS-D78, PS-Mut1, PS-Mut2, Mut 10, Mut11) were analysed. To this end generated IBDV were selected which contain the same reactivity pattern with the used panel of moab. As shown in FIG. 1 growth of virus was influenced by exchange of amino acids in certain regions. Exchange of amino acid 222 from proline to serine showed no influence in growth in cell culture. In contrast, exchange in the region from amino acid 318 to 323 influenced the growth of the investigated mutants. These mutants growth to lower titers at all time points investigated indicating that the region from aa 318 to aa323 is of importance for growth in cell culture.

TABLE 3

Oligonucleotides used in site-directed mutagenesis

| Sequence | Orientation | Position | Amino acid exchange | Name | SEQ ID No. |
|---|---|---|---|---|---|
| GACCATGACATCTGATCCCC TGCCTGACCgtCACTTTTGGA GGTC | anti-sense | 1069-1113 | G318D | Mut1 | 20 |
| GACCATGACATCTGtTCCCCT GCCTGACCgtCACTTTTGGAG GTC | anti-sense | 1069-1113 | G318D D323E | Mut2 | 21 |

TABLE 3-continued

Oligonucleotides used in site-directed mutagenesis

| Sequence | Orientation | Position | Amino acid exchange | Name | SEQ ID No. |
|---|---|---|---|---|---|
| GACCATGACATCTGATCCCC TtCCTGACCgtCACTTTTG-GAG GTC | anti-sense | 1069-1113 | G318D A321E | Mut3 | 22 |
| GACCATGACATCTGtTCCCCT tCCTGACCgtCACTTTTGGAG sense GTC | anti-sense | 1069-1113 | G318D A321E D323E | Mut4 | 23 |
| GACCATGACATCTGtTCCCCT GCCTGACCACCACTTTTGGA GGTC | anti-sense sense | 1069-1113 | D323E | Mut5 | 24 |
| GACCATGACATCTGATCCCC TtCCTGACCACCACTTTTGGA GGTC | anti-sense sense | 1069-1113 | A321E | Mut6 | 25 |
| GACCATGACATCTGtTCCCCT tCCTGACCACCACTTTTGGAG GTC | anti-sense sense | 1069-1113 | A321E D323E | Mut7 | 26 |
| GACCATGACATCTGATCCCC TGCCTGACCgttACTTTTGGA GGTC | anti-sense sense | 1069-1113 | G318N | Mut8 | 27 |
| GACCATGACATCTGtTCCCCT GCCTGACCgttACTTTTGGAG GTC | anti-sense sense | 1069-1113 | G318N D323E | Mut9 | 28 |
| GACCATGACATCTGATCCCC TtCCTGACCgttACTTTTG-GAG GTC | anti-sense sense | 1069-1113 | G318N A321E | Mut10 | 29 |
| GACCATGACATCTGtTCCCCT tCCTGACCgttACTTTTG-GAGG TC | anti-sense sense | 1069-1113 | G318N A321E D323E | Mut11 | 30 |
| ATTGTTACCCCACCGGTTtGg TACTGTGATGAGAATTGG | anti-sense | 772-810 | P222T | P222T | 31 |
| GATTGTTACCCCACCgctTTG GTACTGTGA | anti-sense | 782-811 | P222S | P222S | 32 |
| GTCACTGCTAGGCTCCCagaT GCCGACCATGACATC | anti-sense | 1102-1137 | R330S | R330S | 33 |

TABLE 4

Results of site-directed mutagenesis, transfection experiments and immunofluorescence assay

| Oligo nucleotides[a] | Plasmids[b] | aa-sequence[c] | 57 | R63 | 67 | B69 | Viable | SEQ ID No. |
|---|---|---|---|---|---|---|---|---|
|  | pD78A | GGQAGD | − | + | − | + | + | 1 |
| P222S | pD78A-P222S | GGQAGD | − | + | + | + | + | 1 |
| P222T | pD78A-222T | GGQAGD |  |  |  |  |  | 1 |
| R330S | pD78A-R330S | GGQAGD | − | + | − | + | + | 1 |

TABLE 4-continued

Results of site-directed mutagenesis, transfection experiments and immunofluorescence assay

| Oligo nucleotides[a] | Plasmids[b] | aa-sequence[c] | 57 | R63 | 67 | B69 | Viable | SEQ ID No. |
|---|---|---|---|---|---|---|---|---|
| P222S, R330S | pD78A-P222S-R330S | GGQAGD | − | + | + | + | + | 1 |
| Mut1 | pMut1 | D GQAGD | | + | − | + | + | 3 |
| Mut1, P222S | pMut1-P222S | D GQAGD | | + | + | + | + | 3 |
| Mut1, R330S | pMut1-R330S | D GQAGD | | + | − | + | + | 3 |
| Mut1, P222S, R330S | pMut1-P222S-R330S | D GQAGD | | + | + | + | + | 3 |
| Mut2 | pMut2 | D GQAGE | − | + | − | + | + | 4 |
| Mut2, P222S | pMut2-P222S | D GQAGE | − | + | + | + | + | 4 |
| Mut2, P222T | pMut2-P222T | D GQAGE | | | | | | 4 |
| Mut2, R330S | pMut2-R330S | D GQAGE- | − | + | − | + | + | 4 |
| Mut2, P222S, R330S | pMut2-P222S-R330S | D GQAGE | − | + | + | + | + | 4 |
| Mut3 | pMut3 | D GQEGD | + | − | − | + | + | 7 |
| Mut3, P222S | pMut3-P222S | D GQEGD | | | | | | 7 |
| Mut3, R330S | pMut3-R330S | D GQEGD | − | + | − | + | + | 7 |
| Mut4 | pMut4 | D GQEGE | − | − | − | + | + | 34 |
| Mut4, P222S | pMut4-P222S | D GQEGE | | | | | | 34 |
| Mut4, R330S | pMut4-R330S | D GQEGE | − | − | − | + | + | 34 |
| Mut5 | pMut5 | GGQAGE | − | + | − | + | + | 2 |
| Mut5, P222S | pMut5-P222S | GGQAGE | − | + | + | + | + | 2 |
| Mut5, P222T | pMut5-P222T | GGQAGE | | | | | | 2 |
| Mut5, R330S | pMut5-R330S | GGQAGE | − | + | − | + | + | 2 |
| Mut6 | pMut6 | GGQEGD | + | − | − | + | + | 6 |
| Mut6, P222S | pMut6-P222S | GGQEGD | + | − | − | + | + | 6 |
| Mut6, R330S | pMut6-R330S | GGQEGD | + | − | − | + | + | 6 |
| Mut7 | pMut7 | GGQEGE | − | − | − | + | + | 35 |
| Mut7, P222S | pMut7-P222S | GGQEGE | − | + | − | + | + | 35 |
| Mut7, R330S | pMut7-R330S | GGQEGE | − | − | − | + | + | 35 |
| Mut8 | pMut8 | NGQAGD | − | + | − | + | + | 15 |
| Mut8, P222S | pMut8-P222S | NGQAGD | − | + | − | + | + | 15 |
| Mut8, R330S | pMut8-R330S | NGQAGD | − | + | − | + | + | 15 |
| Mut9 | pMut9 | NGQAGE | − | + | − | + | + | 16 |
| Mut9, P222S | pMut9-P222S | NGQAGE | − | + | + | + | + | 16 |
| Mut9, P222T | pMut9-P222T | NGQAGE | | | | | | 16 |
| Mut9, R330S | pMut9-R330S | NGQAGE | − | + | − | + | + | 16 |
| Mut10 | pMut10 | NGQEGD | + | − | − | + | + | 8 |
| Mut10, P222S | pMut10-222S | NGQEGD | + | − | − | + | + | 8 |
| Mut10, R330S | pMut10-330S | NGQEGD | − | + | − | + | + | 8 |
| Mut11 | pMut11 | NGQEGE | + | − | − | + | + | 9 |
| Mut11, P222S | pMut11-222S | NGQEGE | + | − | − | + | + | 9 |
| Mut11, R330S | pMut11-330S | NGQEGE | − | + | − | + | + | 9 |

[a]Oligonucleotides used for site directed mutagenesis experiments
[b]Obtained mutagenised plasmids used for transfection experiments
[c]Amino acids sequence located at amino acid positions 318-323 is shown in single letter code and exchanged amino acids in comparison to the D78 sequence are bold typed Example 2

Antigenic Properties of the Classic IBDV Mutants

Material and Methods

Characterization of Mutant Virus by Neutralization Assay

To test wether the generated virus was neutralized by monoclonal antibodies neutralization assay was performed essentially as described (Schröder et al., J. Gen. Virol., 81, 533-540, 2000). In brief, 100 µl of a virus solution containing 750 TCID$_{50}$/100 µl was pipetted into each well of a 96 well tissue culture plate with the exception of the first well in each row. Then, 100 µl of either the different moabs (67, B69, 57, R63) or a polyclonal rabbit anti-IBDV serum was pipetted into the empty first well of each row. To the antibody containing wells 100 µl of a virus suspension containing 1500 TCID$_{50}$/100 µl was added then. After mixing virus and serum serial dilutions were made by serially transferring 100 µl/well. After incubation for 1 hour at room temperature 100

µl of QM cells ($10^6$ cells/ml) were added to each well and incubated at 37° C. Six days later wells were scored for the presence of CPE. The end point of the VN-test for a serum sample was determined to be the reciprocal of the highest dilution, expressed in log2, in which no CPE was visible.

Results

Antigenic Properties in Neutralization Asssay

To assay if generated mutants could be neutralized by the appropriate monoclonal antibodies neutralization assays were peformed. For this assay pairs of virus were selected which showed either a different mAb pattern based on one amino acid exchange (D78, PS-D78; Mut1, PS-Mut1; Mut2, PS-Mut2) or the same pattern but different amino acid sequences (D78, Mut1, Mut2; PS-D78, PS-Mut1, PS-Mut2; Mut10, Mut11). The results showed (Table 5) that neutralization occurred in most cases (D78, Mut1, Mut2, PS-D78, PS-Mut1, PS-Mut2, Mut11) in the same pattern as in the fluorescence assay. One exception was Mut 11, which was not neutralized by mAb 57, although it was positive in fluorescence assay indicating that the epitope was present but lost his neutralising property.

TABLE 5

Neutralization assay of IBDV mutants using polyclonal serum and monoclonal antibodies

| Virus[a] | Panel pattern in IIFA[b] | | | | Antibodies used in neutralization assay[c] | | | | anti-IBDV |
|---|---|---|---|---|---|---|---|---|---|
| | 57 | R63 | 67 | B69 | 57 | R63 | 67 | B69 | |
| rD78 | − | + | − | + | $<2^d$ | $>2^{12}$ | $<2$ | $2^{12}$ | $2^{12}$ |
| PS-D78 | − | + | + | + | $<2$ | $>2^{12}$ | $2^{10}$ | $2^{11}$ | $2^{12}$ |
| Mut1 | − | + | − | + | $<2$ | $>2^{12}$ | $<2$ | $2^{10}$ | $2^8$ |
| PS-Mut1 | − | + | + | + | $<2$ | $>2^{12}$ | $2^{11}$ | $2^{10}$ | $2^{10}$ |
| Mut2 | − | + | − | + | $<2$ | $>2^{12}$ | $<2$ | $2^{11}$ | $2^9$ |
| PS-Mut2 | − | + | + | + | $<2$ | $2^{12}$ | $2^{12}$ | $2^{10}$ | $2^7$ |
| Mut10 | + | − | − | + | $2^{11}$ | $<2$ | $<2$ | $2^{10}$ | $2^9$ |
| Mut11 | + | − | − | + | $<2$ | $<2$ | $<2$ | $2^{12}$ | $2^8$ |

[a]recombinant IBDV used in the neutralization assay
[b]results of the panel pattern in the indirect immunflourescence assay using moabs (57, R63, 67, B69) as shown in table 4.
[c]In the neutralization assay four moabs (57, R63, 67, B69) and one polyclonal rabbit anti - IBDV serum.
[d]neutralization titer in $\log_2$ of the diluted serum Example 3

Isolation and Characterisation of the Variant IBDV

Materials and Methods

Isolation of the new IBDV from Bursa Material of Infected Chickens

The new virus (designated with the internal code GB02) was isolated from bursas of diseased animals according to the following procedure:

A chicken flock vaccinated with classic vaccine showed wet litter, general immunosuppression, low weight gain but no high mortality (1-2%). Chickens from this flock were offered for post-mortem examination. Some muscle bleedings were seen and some small bursae. Bursae were isolated, PBS and antibiotics added. Next, the bursae were homogenized with glass pearls and sterile PBS. The homogenates were tested using the Moab panel test. IBDV material that showed a deviating panel pattern was passaged further in animals. 0.1 ml of this homogenate was applied via the in eye-drop route to 14 days old SPF white leghorns. Three-4 days after inoculation the presence of IBDV in the bursa of Fabricius was investigated using the moab panel test.

Primary chicken embryo fibroblasts (CEF) cells were prepared at a final concentration of $2 \times 10^6$/ml. The cells were cultured in Eagles minimum essential medium containing 5% fetal calf serum. To 15 ml of this cell suspension 0.1 ml IBDV isolate GB02 (at passage level 1) was added. After incubation for 3-6 days in a high humidity incubator at 37° C., the supernatant contained the virus strain. A sample of this virus was deposited at the Institute Pasteur, Pads, France under accession no. I-2811. After 2 passages on CEF the virus was further purified by three plaque purification rounds on CEF. Next the virus was cultured in the same way as described above on CEF for 2 rounds. A sample of the plaque purified GB02 isolate (GB02 PP) was deposited at the Institute Pasteur, Paris, France under accession no. I-2925.

IBDV GB02 after 3 plaque purification rounds on CEF was cultured for 2 passages on VERO cells. After the second incubation on VERO cells for 10 days at 37° C. the infected cells suspension was filtered through a sterile cheese cloth.

Antigen-Capture Enzyme Immuno Assay (AC-ELISA)

IBDV was characterised by means of an ELISA using different monoclonal antibodies according to van der Marel et al. (Dtsch. Tierarztl. Wschr. 97, 81-83, 1990):

1. Moab B29 was coated on 96 well microtiterplates. After coating, the plates were washed and the wells of the plates were filled with two- or threefold dilution series of bursal homogenate samples and a standard antigen of known antigenic mass. After incubation and washing of the plates, the plates were incubated with a hyperimmune rabbit anti-IBDV serum. Next the plates were washed again and incubated with conjugate (goat-anti-rabbit immunoglobulin coupled to horse-radish-peroxidase). Finally, the plates were incubated with substrate solution. The enzymatic reaction was stopped with 4N H2SO4. The absorption in the wells was read at 450 nm with an ELISA reader. The antigenic mass content of the bursal samples relative to the standard antigen was calculated by regression analysis. The antigenic content of the bursal samples is expressed as B29 EU/ml.

2. The subsequent procedure was similar to the one described for the B29 ELISA with the exception of: 1. The plates were coated with different Moabs, 2. The bursa homogenate samples were diluted to a concentration of 5000 B29 EU/ml. Then a single dilution was dispensed in the wells coated with the different Moabs. The subsequent steps were the same as for the B29 ELISA.

3. The absorption ratios were calculated according to the following formula $$\text{Ratio} = \frac{E450\ Moab\ \text{``}X\text{''} - E450\ \text{background of }Moab\ \text{``}X\text{''}}{E450\ Moab\ B29 - E450\ \text{background of }Moab\ B29}$$

The ratios are classified as follows:

| Ratio | reactivity | explanation |
|---|---|---|
| 0-0.3 | − | Moab does not bind to virus strain |
| 0.3-0.7 | 0 | reduced Moab binding to virus strain |
| >0.7 | + | complete Moab binding to virus strain |

Cloning and Sequencing of Segment A of the Variant IBDV

Material and Methods

Purification of Viral RNA.

Obtained bursae of chicken were homogenized. The homogenate was centrifuged at 13000×g for 5 min to eliminate cellular debris. One volume of chloroform were added to the obtained supernatant and vortexed. After centrifugation at 13000×g for 5 min to the resulting supernatant proteinase K and sodium dodesylsulphate was added to a final concentration of 1 mg/ml and 0.5%, respectively, and incubated at 56° C. for 1 hour. Nucleic acids were obtained after extraction of the digested proteins using one volume phenol/chloroform. After one additional phenol extraction using one volume chloroform nucleic acids were precipitated by adding of 1/10 volume of 3M sodium acid (pH5.2) and 2.5 volume absolute ethanol.

Construction of a cDNA Clone Comprising Segment.

For cloning of the cDNA of segment A the purified RNA was reverse transcribed into cDNA, and amplified by polymerase chain reaction (PCR) following standard procedures using the methods as described by Mundt and Vakharia (PNAS 93, 11131-11136, 1996).

Appropriate primer pairs (BelgFP/BelgRP nucleotides 608-629 and 1201-1222) were added to dissolved nucleic acids. The primer-nucleic acid mixture was added to the reaction mixture [reaction buffer (Invitrogen), DTT (Invitrogen), dNTP mixture (Promega), Superscript II (Invitrogen)].

The amplification of the appropriate cDNA fragments were performed using the primer pair BelgFP/BelgRP resulting in the RT-PCR fragment BelgApart. The PCR was performend by using Deep Vent polymerase (New England Biolabs) and 2 µl of the RT-reaction.

Amplification product was cloned blunt ended and plasmids containing appropriate PCR fragments were sequenced. The cloning procedure to obtain a plasmid containing the segment A under control of the T7-RNA polymerase promotor corresponded to the procedure described by Mundt and Vakharia (1996, supra).

Three plasmids resulting from cloning of each PCR fragment (pBelgApart) were analysed by sequencing of the DNA in both directions. Cloned PCR fragments were sequenced and obtained sequences were analysed using the Wisconsin package, Version 8 (Genetics Computer Group, Madison, Wis., USA).

The amino nucleotide sequence as well as amino acid sequence alignments were performed using ClustalW.

Virus Neutralisation (VN) Assay

This experiment was conducted to assess the antigenic relatedness of IBDV GB02 with the known reference IBDV strains. Sera collected after infection of three-week-old SPF chickens with IBDV GB02 were examined in a virus neutralisation test against IBDV GB02, the classical type IBDV D78 and the American variant types IBDV VarE and IBDV GLS-5.

One group of 13 three-week-old SPF chickens were infected with IBDV GB02 via oculo-nasal route. Before the start of the experiment and at 4 weeks post infection blood samples were collected from all chickens. Sera were examined for the absence/presence of IBDV antibodies in a virus neutralisation (VN) test.

Sera were examined for the presence/absence of IBDV antibodies in a virus neutralisation test according to the procedure outlined below.

Serial two-fold dilutions of the sera were mixed with an equal volume of virus suspension containing approximately 750 $TCID_{50}$ of IBDV D78, IBDV GB02, IBDV VarE or IBDV GLS-5. Following incubation for 90 minutes at +37° C. chicken embryo fibroblasts (CEF) were added. The antibody titres were established after 5 days of incubation at +37° C. by microscopical examination of the CEF monolayers for the presence/absence of CPE characteristic of IBDV. Antibody titres were the reciprocal of the highest dilution in which IBDV was neutralised completely. Serum samples with titres of <4 ($log_2$) were considered negative for IBDV antibodies.

Results

AC-ELISA

A new immunogenic variant IBDV was isolated from the bursa material. This virus was designated isolate GB02. The panel pattern for this new variant IBDV isolate is shown in Table 6A. Results of controls samples are given in Table 6B.

TABLE 6A

Panel pattern of new variant IBDV with different moabs.

| Sample | Moab | | | | | | | |
|---|---|---|---|---|---|---|---|---|
| | 8 | R63 | B69 | 10 | BK9 | 67 | 57 | 44A1 |
| GB02 | + | + | + | + | − | + | − | ND |

TABLE 6B

Panel pattern of different IBDVs with different moabs.

| Controls↓/Moab→ | 8 | R63 | B69 | 10 | BK9 | 67 | 57 | 44A1 |
|---|---|---|---|---|---|---|---|---|
| Classic (F52/70) | + | + | + | + | − | − | − | + |
| Variant-E | + | + | − | − | + | + | − | + |
| GLS | + | − | − | + | − | − | + | + |

+epitope present on virus,
−epitope not present on virus.
ND = not done.

From Tables 6A and 6B it can be seen that the newly isolated IBDV reacted in a different way with the different monoclonal antibodies than the control samples. The new virus reacts with both Moab10 and Moab 67. Moab 10 normally reacts with classic and GLS-like strains but never in combination with variant-E-like viruses. Moab 67 reacts only with variant-E-like viruses and never with classic and GLS-like viruses. The combination of Moab 10 and 67 present on the same virus at the same time is a unique combination, indicating that the isolated virus is a new IBDV variant.

Sequence Data

Furthermore, a cDNA clone comprising the VP2 gene of the new variant IBDV was generated and sequenced. The nucleotide sequence and the deduced amino acid (aa) sequence is shown in SEQ ID No. 36 and 37.

It is known that the epitopes that specifically react with the various moabs are located on the VP2 protein, in particular, in the so-called variable regions that generally spans amino acids 212 to 332 (see Vakharia et al., 1994, supra).

The obtained partial nucleotide sequence of segment A was compared with sequences of different strains of IBDV (Table 7).

TABLE 7

```
                                                                       [SEQ ID NO:37]
             174       184       194       204       214       224

GB02    VLSLPTSYDLGYVRLGDPIPAIGLDPKMVATCDSSDRPRVYTITAADDYQFSSQYQSGG 52-70   ---------------------------------------------------P--

002-73  ---------------------------------------------------P--

UK661   ---------------------------------------------------A--

Var-A   ---------------------------------------------------Q--

Var-E   ----------------------------------------N--------T--

GLS     -------------------------------------------------T--

234       244       254       264       274       284

GB02    VTITLFSANIDAITSLSIGGELVFHTSVQGLALNATIYLIGFDGTTVITRAVASDNGLTT 52-70   ------------------------Q------V-G----------A-------A-----A 002-73  ---------------N-V-------Q------V--------V-------T-----AG----A

UK661   ------------------------Q------I-G----------A-------A-----A

Var-A   -----------------V------K----S-V-G----------A-------AN----A

Var-E   -----------------V------K----S-V-G----------A-------AN----A

GLS     -----------------V------K---HS-V-G----------SA--------AN-----

294       304       314       324       334       344

GB02    GIDNLMPFNLVIPTNEITQPITSIKLEIVTSKSGGQAGDQMSWSASGSLAVTIHGGNYPG 52-70   -T----------------------------------------------------------

002-73  -T------------S-----V--------------------L---N------------

UK661   -T--------I----S--------------------------------------------

Var-A   -------------------------------D------------------------

Var-E   -------------------------------D----E--------------------

GLS     -T----------------------------------------------------------

354

GB02    ALRPVTLVAYER 52-70   ------------

002-73  ------------

UK661   ------------

Var-A   ------------

Var-E   ------------

GLS     ------------
```

Alignment of amino acid sequences of different serotype I strains of IBDV. The partial amino acid sequence of the belgium GB02 isolate encoded by the polyprotein gene of segment A was aligned with sequences of the Variant E strain (Var-E: Genbank accession number X54858), Variant A strain (Var-A: M64285), the australian strain 002-73 (Nucleic Acids Research, 1986, 12, pp. 5001-5012), the very virulent strain UK661 (AJ318896), the classical strain Faragher 52-70 (D00869), and the variant strain GLS (M97346). The numbering of the amino acid sequence in in accordance to Mundt and Müller (supra, 1995).

The compared region showed a variety of amino acid exchanges to all sequences used for the sequence comparison. This is further evidence that the newly isolated virus represents a new type of IBDV not described so far. The highest number of exchanges was detected in the VP2 variable region (aa 212-332). The comparison of the percentage homology of the nucleotide- and amino acid sequences (92.3% to 95.9%) showed that the sequences of the new virus were as much different to the subtypes of IBDV as the subtypes were different to each other.

VN Assay

No antibodies to IBDV D78, IBDV GB02, IBDV VarE and IBDV GLS-5 could be detected in the sera obtained before the start of the experiment.

The mean IBDV antibody titres determined in the sera collected 4 weeks post infection are outlined in the table below:

TABLE 8

| | Mean $\log_2$ IBDV VN antibody titre (standard deviation) at 4 weeks post infection to . . . | | | |
|---|---|---|---|---|
| Inoculum | IBDV D78 | IBDV GB02 | IBDV VarE | IBDV GLS-5 |
| IBDV GB02 1st chicken passage batch 21D02 | 10.9 (2.5) | ≧16.5 (0.9) | 8.3 (2.3) | 8.9 (2.1) |

These results show that following infection with IBDV GB02, the antibody response to IBDV GB02 is significantly higher than the antibody responses to IBDV D78, IBDV VarE and IBDV GLS-5. This indicates that IBDV GB02 is antigenically different from the classical type IBDV D78 and from the American variant types IBDV Var E and IBDV GLS-5.

Example 4

Vaccination of Chickens with a Vaccine Based on the Variant IBDV

Experimental Design

Two groups of 20 three-week-old SPF chickens were vaccinated with inactivated variant IBDV vaccine or inactivated classical IBDV vaccine. Another group of 20 three-week-old SPF chickens was not vaccinated to serve as control. At 6 weeks post vaccination, all vaccinated and control chickens were subjected to a challenge with the IBDV variant field isolate. At four days post challenge the bursae were removed and examined for the presence/absence of IBDV variant challenge virus in an antigen capture ELISA.

Before the start of the experiment blood samples were collected from 20 chickens. At 2, 4 and 6 weeks post vaccination blood samples were collected from all chickens individually. Sera were examined for the absence/presence of IBDV antibodies in a virus neutralisation (VN) test.

Materials and Methods

IBDV Variant Vaccine

Variant IBDV (isolate GB02) was produced on VERO cells and subsequently inactivated with formaldehyde. The inactivated IBDV GB02 antigen was emulsified in a W/O emulsion so that each dose contained 10 EU (R63 ELISA based) of IBDV GB02. Chickens were vaccinated each with 0.5 ml of the IBDV GB02 vaccine via intramuscular route in the leg muscle.

IBDV Classical Vaccine

Classical IBDV (strain D78) was produced on VERO cells and subsequently inactivated with formaldehyde. The inactivated IBDV D78 antigen was emulsified in a W/O emulsion so that each dose contained 10 EU (R63 ELISA based) of IBDV D78. Chickens were vaccinated each with 0.5 ml of the IBDV D78 vaccine via intramuscular route in the leg muscle.

Challenge Material

IBDV GB02 was plaque purified on CEF and subsequently passaged in SPF chickens. Chickens were challenged each with a calculated infectivity titre of $10^{5.1}$ TCID$_{50}$ of GB02 challenge virus via the ocular route.

Serology

Sera were examined for the presence/absence of IBDV antibodies in a virus neutralisation test according to the procedure outlined below.

Serial two-fold dilutions of the sera were mixed with an equal volume of virus containing approximately 750 TCID$_{50}$ of either IBDV D78 or IBDV GB02. Following incubation of 90 minutes at +37° C. chicken embryo fibroblasts (CEF) were added. The antibody titres were established after 5 days of incubation at +37° C. by microscopical examination of the CEF monolayers for the presence/absence of CPE characteristic of IBDV. Antibody titres were the reciprocal of the highest dilution in which the IBDV was neutralised completely. Serum samples with titres of <4 ($\log_2$) were considered negative for IBDV antibodies.

Antigen Capture ELISA

Two dilutions (1:2 and 1:4) of the bursa homogenates were added to IBDV monoclonal antibody MCA 67 absorbed onto a microtitre plate. Following incubation of 1.5 hours at +37° C., the presence of IBDV GB02 challenge virus bound to MCA67 was detected by adding IBDV monoclonal antibody MCA8 coupled to horse radish peroxidase. Samples with absorbance values higher than 2 times the mean back ground value were considered positive for IBDV GB02 challenge virus.

Results and Discussion

Serology

No antibodies to IBDV D78 and IBDV GB02 could be detected in the sera obtained before the start of the experiment.

The mean IBDV antibody titres determined in the sera collected at 2, 4 and 6 weeks post vaccination outlined in the table below:

TABLE 9

| | Mean IBDV VN antibody titre (standard deviation) at ... weeks post vaccination | | | | | |
|---|---|---|---|---|---|---|
| | 2 wks | | 4 wks | | 6 wks | |
| Inoculum | D78 | GB02 | D78 | GB02 | D78 | GB02 |
| IBDV D78 (10 EU/dose) | 3.8 (1.3) | <4.0 (0.0) | 11.6 (3.2) | 6.0 (2.4) | 12.8 (2.9) | 6.0 (2.3) |
| IBDV GB02 (10 EU/dose) | 5.8 (2.2) | 6.3 (1.3) | 9.4 (2.4) | 12.0 (2.3) | 9.7 (1.6) | 14.0 (2.5) |
| Controls (no inoculation) | <4.0 (0.0) | <4.0 (0.0) | <4.0 (0.0) | <4.0 (0.0) | <4.0 (0.0) | <4.0 (0.0) |

These results show that both the inactivated IBDV D78 vaccine and the inactivated IBDV GB02 vaccine provoke an immune response following vaccination of three-week-old SPF chickens. Following vaccination with the classical inactivated IBDV D78 vaccine, the cross neutralisation test revealed a relatively large difference in mean antibody titre against the homologous IBDV D78 antigen and the heterologous GB02 antigen. The latter indicates that the new variant IBDV is not antigenically related to the classical IBDV.

Detection of IBDV Challenge Virus in the Bursa by an Antigen Capture ELISA

Results obtained with the detection of challenge virus in the bursae removed at 4 days post challenge are outlined in the table below.

TABLE 10

| Inoculum | Percentage of bursae in which IBDV challenge virus was detected |
|---|---|
| IBDV D78 (10 EU/dose) | 40% |
| IBDV GB02 (10 EU/dose) | 0% |
| Controls (no inoculation) | 90% |

The results show that after challenge with the IBDV GB02 field isolate no challenge virus could be detected in any of the bursae derived from the chickens vaccinated with the inactivated IBDV GB02 vaccine. On the other hand, IBDV GB02 challenge virus could be detected in 40% of the bursae derived from chickens vaccinated with the inactivated IBDV D78 vaccine.

As the bursa is considered the predilection site of virus replication for IBDV, the results obtained in this experiment indicate that the inactivated IBDV GB02 vaccine provides chickens with a solid protection against infection with the IBDV GB02 field isolate.

Thus, the results indicate that a vaccine based on a classical IBDV does not provide chickens with a solid protection against infection with the new variant IBDV.

The invention claimed is:

1. A classic infectious bursal disease virus (IBDV) mutant that expresses a VP2 protein that binds with monoclonal antibody (moab) B69, wherein the VP2 protein also binds with moab 67, secreted by hybridoma cell lines HB-9437 and HB-11122, deposited at the ATCC, Rockville, USA, respectively, wherein the mutant comprises one or more mutations in a classic VP2 coding region, such that the coding region comprises,
   (i) a codon for the amino acid at position 222 encoding an amino acid selected from the group consisting of serine and threonine, and
   (ii) a nucleotide sequence encoding an amino acid sequence selected from the group consisting of SEQ ID. No. 2, SEQ ID. No. 3, SEQ ID. No. 4 and SEQ ID. No. 5 at positions 318-323.

2. A classic IBDV mutant according to claim 1, wherein the coding region comprises a codon for the amino acid at position 330 encoding an amino acid selected from the group consisting of arginine and serine.

3. The classic IBDV mutant according to claim 1, wherein the mutant comprises one or more mutations in a VP2 coding region of IBDV strain D78.

4. The classic IBDV mutant according to claim 1, wherein the mutant comprises a genomic segment A of IBDV strain D78.

5. An immunogenic composition for raising antibodies in poultry against IBDV comprising a classic IBDV mutant according to claim 1, together with a pharmaceutically acceptable carrier or diluent.

6. The immunogenic composition according to claim 5, wherein the classic IBDV mutant is in a live form.

7. The immunogenic composition according to claim 5, which further comprises one or more of other pathogens infectious to poultry.

8. The immunogenic composition according to claim 5, which comprises an adjuvant.

9. A classic infectious bursal disease virus (IBDV) mutant that expresses a VP2 protein that binds with monoclonal antibody (moab) B69, wherein the VP2 protein also binds with moab 67, secreted by hybridoma cell lines HB-9437 and HE-11122, deposited at the ATCC, Rockville, USA, respectively, wherein the mutant comprises one or more mutations in a classic VP2 coding region, such that the coding region comprises,
   (i) a codon for the amino acid at position 222 encoding threonine, and
   (ii) a nucleotide sequence encoding an amino acid sequence selected from the group consisting of SEQ ID. No. 1, SEQ ID No. 2, SEQ ID No. 3, SEQ ID. No. 4, and SEQ ID No. 5 at positions 318-323.

10. The classic IBDV mutant according to claim 9, wherein the coding region comprises a codon for the amino acid at position 330 encoding an amino acid selected from the group consisting of arginine and serine.

11. The classic IBDV mutant according to claim 9, wherein the mutant comprises one or more mutations in a VP2 coding region of IBDV strain D78.

12. The classic IBDV mutant according to claim 9, wherein the mutant comprises a genomic segment A of IBDV strain D78.

13. An immunogenic composition for raising antibodies in poultry against IBDV comprising a classic IBDV mutant according to claim 9, together with a pharmaceutically acceptable carrier or diluent.

14. The immunogenic composition according to claim 13, wherein the classic IBDV mutant is in a live form.

15. The immunogenic composition according to claim 13, which further comprises one or more immunogens of other pathogens infectious to poultry.

16. The immunogenic composition according to claim 13, which comprises an adjuvant.

* * * * *